United States Patent [19]

Venkatasetty

[11] Patent Number: 4,662,996
[45] Date of Patent: May 5, 1987

[54] METHOD AND ELECTROCHEMICAL SENSOR FOR SENSING CHEMICAL AGENTS USING A SENSING ELCTRODE COATED WITH ELECTRICALLY CONDUCTIVE POLYMERS

[75] Inventor: H. V. Venkatasetty, Burnsville, Minn.

[73] Assignee: Honeywell Inc., Minneapolis, Minn.

[21] Appl. No.: 811,542

[22] Filed: Dec. 20, 1985

[51] Int. Cl.$^4$ ............................................. G01N 27/52
[52] U.S. Cl. .................................... 204/1 T; 204/400; 204/412; 204/414; 204/415; 204/431; 204/432
[58] Field of Search ............... 204/412, 414, 415, 431, 204/432, 1 F, 1 K, 1 N, 1 T, 400

[56] References Cited

U.S. PATENT DOCUMENTS 4,522,690  6/1985  Venkatasetty ...................... 204/1 T

OTHER PUBLICATIONS

A. H. Schroeder, et al; Electrochemistry and Conductivity of New Tractable Electrically Conducting Polymers, Extended Abstracts, The Electrochemical Society, vol. 83-1, Spring Meeting, May 8-13, 1983.
Y. S. Papir, et al; Synthesis and Chemical Doping of New Tractable Electrically Conducting Polymers, Extended Abstracts, The Electrochemical Society, vol. 83-1, Spring Meeting, May 8-13, 1983.

Primary Examiner—G. L. Kaplan
Attorney, Agent, or Firm—Charles G. Mersereau

[57] ABSTRACT

An electrochemical method and apparatus for detecting polar toxic species is disclosed which uses a conductive polymer coated sensing electrode. The conductive polymers may be polyquinoline or substituted polyquinolines.

20 Claims, 3 Drawing Figures

METHOD AND ELECTROCHEMICAL SENSOR FOR SENSING CHEMICAL AGENTS USING A SENSING ELCTRODE COATED WITH ELECTRICALLY CONDUCTIVE POLYMERS

BACKGROUND OF THE INVENTION

1. Field of the Invention

The present invention relates generally to the detection of toxic species and, in particular, to a method and apparatus for detecting polar chemical agents and toxic species using conductive polymer coated sensing electrodes which exhibit renewable sensing characteristics enabling many repeated uses.

2. Description of the Prior Art

Electrochemical reactions based on oxidation or reduction (Redox) of metals and compounds at an electrode are highly selective because of the characteristic Redox potential at which the oxidation or reduction of the electroactive species occurs. With electrochemical sensing, selection of the electrode material and electrolyte solution is very important in determining sensitivity and selectivity. Theoretical considerations for Redox electrochemistry are developed in more detail below.

An electrochemical cell utilized for the detection of toxic species normally consists of a working or sensing electrode, counter electrode and a reference electrode situated such that an adjustable potential source may be connected across the sensing and counter electrodes and the current measured. This system includes an electrolyte solution containing a solvent and an electrolyte material together with a depolarizer, if desired. The solvent and electrolyte solutions from such solvents should be electrochemically stable to oxidation and reduction in the operating range of the electrochemical cell. This is necessary to give the widest possible voltage window to carry out electrochemical Redox reactions at the electrode surface without causing the decomposition of the solvent. Thus, the oxidation and/or reduction potentials of the sensing electrode must be lower than the decomposition potential of the electrolyte solvent.

One such cell which utilizes a non-aqueous, aprotic electrolyte system and includes a platinum sensing electrode is illustrated and described in U.S. Pat. No. 4,555,690 to H. V. Venkatasetty, the inventor of the present invention. That application is assigned to the same assignee as the present application.

Conducting polymeric materials are also known in the prior art and certain conducting polymers have also been utilized in fabricating polymer-coated platinum wire electrodes. Properties of certain polyquinoline polymers and substituted polyquinoline polymers as conductors together with their use as coatings on platinum electrodes are discussed by A. H. Schroeder, et al and Y. S. Papir, et al, respectively in abstracts numbers 543 and 544 of the Extended Abstracts of the Electrochemical Society, Spring Meeting, 1983.

Although prior art sensors have been quite successful in detecting chemical agents and toxic chemicals of interest, electrochemical cells of the type described in the above-referenced U.S. Patent use platinum sensing electrodes whereas in the present invention a variety of sensing electrodes are available. Thus, one may choose the most sensitive one for detecting a particular chemical of interest. Each polymer coated electrode has its own characteristic voltammogram related to the particular polymer used. The pure platinum electrode by itself, however, does not have well defined voltammogram.

SUMMARY OF THE INVENTION

By means of the present invention, the problems associated with renewal or regeneration and tailoring of the Redox potential of electrochemical sensors of polar chemical agents and toxic species of interest has been solved by the provision of a method and apparatus which utilizes the properties of certain conductive polymers to produce a highly reversible and tailorable sensing system.

In the preferred embodiment a thin film of a conductive polymer, preferably a polyquinoline or substituted polyquinoline polymer such as poly-2,6-(4 phenyl) quinoline is coated on a noble metal wire, such as a platinum wire, to produce the sensing electrode. A counter electrode of the same noble metal and a reference electrode of silver/silver ion (Ag/Ag+) are used. Because the Redox potential of the conducting polymers are normally higher than the decomposition potential of water and because most chemical agents and toxic species of interest dissolve more readily in organic solvents, the electrochemical cell utilizes a nonaqueous aprotic electrolyte solution such as lithium perchlorate in propylene carbonate/$\gamma$-butyrolactone or a solution of tetrabutyalammonium perchlorate and acetonitrile.

These conducting polymer films show highly reversible electrochemical Redox behavior which is very sensitive to interactive chemicals present in the environment. Toxic chemicals and/or vapors on adsorbing on the electrode change the Redox potential of the sensor cell when the potential is applied to the sensing electrode. This change in potential is characteristic of the chemical species to be sensed and the current generated during Redox process is proportional to the concentration of that chemical species. The Redox potential of the coated electrode can be fine-tuned by chemical modification of the coating with corresponding change in the electrical conductivity. This is accomplished by attaching various electron withdrawing and donating groups to the pendant phenyl ring to raise and lower the Redox potential.

The polymers are readily processable and can be conveniently used to coat noble metal or carbon electrodes. Cells utilizing the conductive polymer-coated electrodes and appropriate aprotic organic solvents can be used as probes for detecting various polar chemical agent species and toxic gases or vapors such as CO, $NO_x$, HCHO, etc.

THEORETICAL CONSIDERATIONS FOR REDOX ELECTROCHEMISTRY

Figure 1:
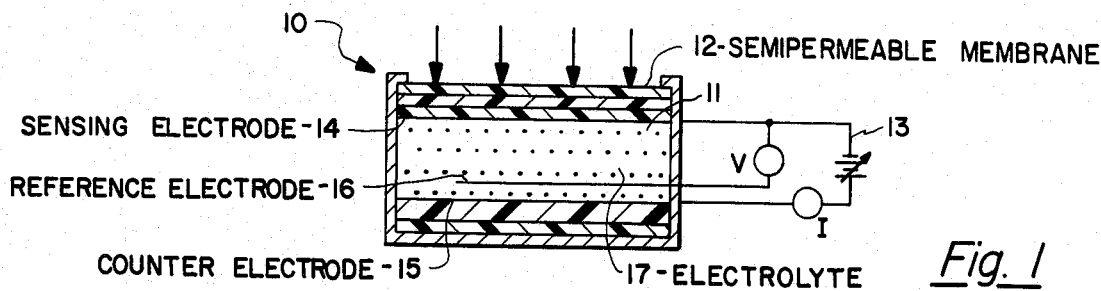
FIG. 1 depicts a schematic diagram of an electrochemical cell which can be used in the system of the invention.

Prior to the detailed description, a brief recap of the theoretical considerations for Redox electrochemistry as pertinent to this invention will be presented.

Considering a general electrochemical reaction where the species O undergoes reduction to species R.

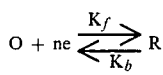
$$O + ne \underset{K_b}{\overset{K_f}{\rightleftarrows}} R \quad (1)$$

In this reduction reaction, $K_f$ represents the forward rate constant (reduction) and $K_b$ represents the reverse rate constant (oxidation). For the electrode process involving the species O and R, the rate expression can be written in the form $$\frac{-dN_O}{dt} = \frac{dN_R}{dt} = K_f(O) - K_b(R) \quad (2)$$

where $N_O$ and $N_R$ are the number of moles of O and R reacting per unit area per unit time. Taking into consideration the effect of applied potential to the electrode, namely the overpotential $\eta = E - E_O$ where E is the operating potential and $E_O$ is the equilibrium potential, the rate constant for the forward reduction reaction is given by $$K_f = K_o e^{-\alpha \eta F/RT} \quad (3)$$

and the rate constant for the oxidation reaction is given by $$K_b = K_o e^{\frac{(1-\alpha)\eta F}{RT}} \quad (4)$$

where $K_O$ is the rate constant at $E = E_O$, R = gas constant, and T = absolute temperature °K.

In electrochemical reaction, the rate constant can be related to current density and the net rate given by $i = i_c - i_a$, where i is the net rate and $i_c$ is the current density representing forward rate and $i_a$ is the current density representing oxidation reaction.

Therefore, the net current density of an electrochemical reaction can be represented by the Butler-Volmer equation:

$$i = i_o \left[ \exp\frac{-\alpha \eta F}{RT} - \exp(1-\alpha)\frac{\eta F}{RT} \right] \quad (5)$$

where i is the net current density, $i_o$ is the exchange current density, $\alpha$ is the symmetry factor, F is the Faraday constant, $\eta$ is the over potential, and R and T have the usual significance.

Depending on the magnitude of overpotential, the anodic or cathodic reaction predominates in reactions involving practical applications of electrochemical techniques.

For electrochemical oxidation processes involving appreciable overpotentials ($\eta > 50$ mV), $$i = i_o \exp[1 - \alpha)\eta F/RT], \quad (6)$$

$$\ln i = \ln i_o + \frac{(1-\alpha)\eta F}{RT} \quad (7)$$

$$= -\frac{RT}{(1-\alpha)F} \ln i_o + \frac{RT}{(1-\alpha)F} \ln i, \quad (8)$$

and $\eta = A + B \ln i$ which is the well known Tafel equation.

Similarly, for electrochemical reduction involving appreciable overpotential, $$i = -i_o \exp(-\alpha \eta F/RT), \quad (9)$$

$$\text{and } \ln i = -\ln i_o - \frac{\alpha \eta F}{RT} \quad (10)$$

For electrochemical processes involving large overpotential, as in practical devices, mass transport of electroactive species to the sensing electrode material becomes the controlling factor. The mass-transfer processes responsible for bringing the electroactive species to the surface of the sensing electrode are diffusion controlled under the influence of a concentration gradient, migration of charged ions in an electric field and convection due to motion of the solution. One can eliminate mass transport by migration by using a high concentration of an inert supporting electrolyte, convection can be minimized by using unstirred vibration-free solution. Under these conditions, the limiting current is controlled solely by diffusion of the reacting species through the concentration gradient adjacent to the electrode. The net rate of diffusion of the species to a unit area of electrode surface at any time, t, is proportional to the magnitude of the concentration gradient. It can be represented by Fick's law of diffusion.

$$\text{Flux} = -D\frac{(dc)}{dx_{x=o}} = \frac{-D(C_{bulk} - C_o)}{\delta} \quad (11)$$

where D is the diffusion coefficient of the species, and $\delta$ is the diffusion layer thickness about the sensing electrode. At appreciably high overpotential, the region around the sensing electrode becomes depleted of electroactive species, i.e, as the $C_e$ approaches zero, the rate of diffusion becomes proportional to the concentration in the bulk of the solution, $C_{bulk}$. At equilibrium, the rate of discharge of the ions is equal to the rate of diffusion to the electrode. The rate of discharge of electroactive species is equal to $i/nF$ where i is the Fardaic current density, n is the number of electrons involved and F is the Farday constant.

$$\text{Flux} = \frac{i}{nF} = D\frac{(dc)}{dx_{x-o}} = \frac{D(C_{bulk} - C_o)}{\delta} \quad (12)$$

$$i_1 = \frac{\eta FDC_{bulk}}{\delta} \quad (13)$$

where $i_1$ = limiting current density.

In this expression the ratio $D\delta$, called the mass transfer coefficient of electroactive species, depends on the electrode geometry, the flow velocity, the diffusion coefficient of the species and the Kinematic viscosity of the electrolyte solution. These parameters can be otimized for maximum current density.

DESCRIPTION OF THE PREFERRED EMBODIMENT

FIG. 1 illustrates an electrochemical cell 10 consisting of a chamber 11 which is accessible to species of interest as through a semipermeable membrane 12. The chamber 11 contains a working or sensing electrode 14, a counter electrode 15 and a reference electrode 16. The working electrode is normally of platinum but may be of carbon or other suitable material. The working electrode is coated with a thin film of a conducting polymer in accordance with the present invention. The counter electrode is of the same material as the sensing electrode and the reference electrode is normally the well-known standard silver/silver ion (Ag/Ag+).

Figure 1A:
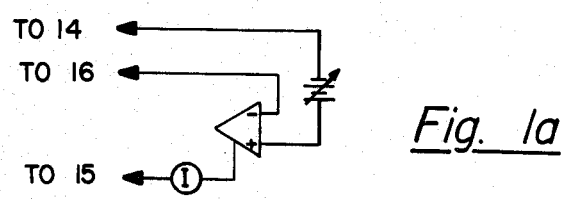
FIG. 1a is a preferred form of an energizing circuit for the electrochemical cell of FIG. 1

An adjustable potential source 13 is connected across the sensing and counter electrodes and the current is measured in this circuit. A voltage exists but no current flows from the reference electrode to the sensing electrode. A preferred form of this energizing circuit may include an operational amplifier as shown in FIG. 1a wherein no current flows in the feedback loop from the reference electrode to the negative input of the operational amplifier.

The three electrodes are internally separated by a material which also acts as a wicking material for the electrolyte. A gelled nonaqueous electrolyte solution 17 permeates and fills the chamber. Because the conducting polymer electrode surface of the working or sensing electrode 14 has an oxidation and/or reduction potential (see Table I) which is higher than the decomposition potential of water (1.23 V), it is necessary to use an aprotic organic electrolyte based system which has an oxidation or reduction potential above that of the conducting polymer composition, i.e. about 2.0 V. One such solution utilizes an aprotic organic solvent such as propylene carbonate or γ-butyrolactone and an active electrolyte such as lithium perchlorate ($LiClO_4$) which has a wide potential window so that gases sought to be detected can be oxidized or reduced in the presence of the conducting polymer without decomposing the electrolyte solution.

It is well known that most toxic gases or vapors such as CO, $NO_2$, HCHO and the vast majority of other chemical agents are polar compounds. In accordance with the present invention, it has been found that such polar compounds absorb preferentially on the surface of conducting polymers such as polyquinolines and substituted polyquinolines. In so doing, they change the surface properties and the Redox potential of the conducting polymer surface electrode. When the potential is applied across the electrode, the absorbed toxic material is oxidized or reduced, depending on the species, to nonpolar product(s) (e.g. CO $CO_2$). The species then desorbs from the electrode into the electrolyte solution thereby rejuvinating the electrodes for subsequent sensing of gases.

Figure 2:
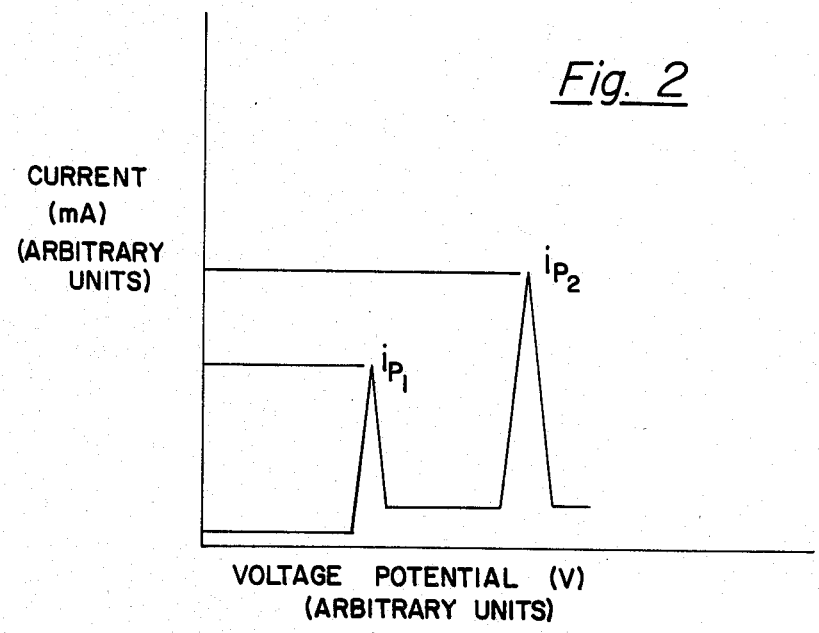
FIG. 2 is a graphical representation of possible cell responses to a pair of toxic species.

If two or more toxic species are present in the gas exposed to the cell, because of their inherent molecular structure differences, they undergo oxidation or reduction at different but characteristic potentials. Hence, as illustrated in FIG. 2, they can be distinguished in their potential and their concentration by the difference in the amount of current which flows.

Table I depicts some of the compounds which may be used to coat the sensing electrode in accordance with the invention. The variance in Redox potential further allows tailoring of electrodes for the improved detection of particular species of interest.

TABLE I
Effect of chemical structure on conductivity and redox potential of polyquinolines.

| POLYMER | CONDUCTIVITY S/cm | REDOX POTENTIAL EVs SCE |
|---|---|---|
| 1 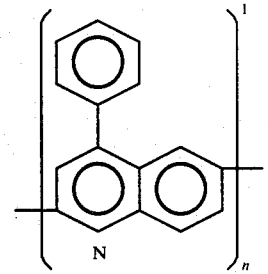 | 50 | −1.65 |
| 2 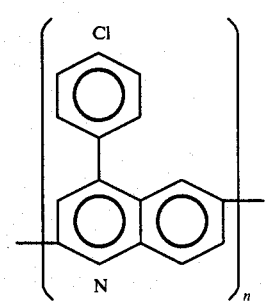 | 1.3 | −1.60 |
| 3 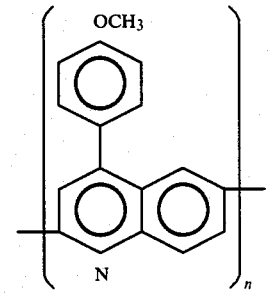 | 4.5 | −1.75 |
| 4 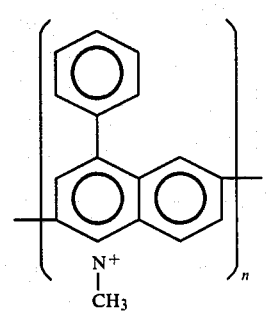 | 0.93 | −0.9 |

1 Poly-2,6-(4-phenyl) quinoline
2 Poly-2,6-(4-chlorophenyl) quinoline
3 Poly-2,6-(4-methoxyphenyl) quinoline
4 Poly-2,6-(N—methyl, 4-phenyl) quinoline The embodiments of the invention in which an exclusive property or right is claimed are defined as follows:

1. A method of detecting the presence of polar chemical agents or toxic species of interest comprising the steps of:
providing an electrochemical cell means including energizing means having an electrode configuration comprising a plurality of electrodes including a noble metal counter electrode, an Ag/Ag+ reference electrode and a working electrode further comprising a core of the same noble metal as the counter electrode coated with a layer of a conducting polymer having reversible Redox characteristics, said cell further including a nonaqueous gelled aprotic electrolyte solution in the electrochemical cell means, said solution comprising an aprotic organic solvent and an electrolyte salt;

exposing the electrochemical cell means to an atmosphere suspected of containing a species of interest;

measuring the potential between the working and reference electrodes to identify the species of interest; and measuring the current flowing between said sensing electrode and said counter electrode to determine the concentration of said species of interest.

2. The method of claim 1 wherein said noble metal is platinum.

3. The method of claim 1 wherein said electrolyte solvent is one selected from the group consisting of γ-butyrolactone and propylene carbonate, and wherein said electrolyte salt is lithium perchlorate.

4. The method of claim 1 wherein said conducting polymer is one selected from the group consisting of polyquinoline and substituted polyquinolines.

5. The method of claim 4 wherein said substituted polyquinoline is selected from the group consisting of poly-2,6-(4-phenyl) quinoline, poly-2,6-(4-chlorophenyl) quinoline, poly-2,6-(4-methoxyphenyl) quinoline, and poly-2,6-(N-methyl, 4-phenyl) quinoline.

6. The method of claim 5 wherein said substituted polyquinoline is poly-2,6-(4-phenyl) quinoline.

7. The method of claim 5 wherein said noble metal is platinum and said electrolyte said is lithium perchlorate.

8. The method of claim 7 wherein said substituted polyquinoline is poly-2,6-(4-phenyl) quinoline.

9. An electrochemical sensor for gaseous or vaporous chemical agents or toxic species detection comprising:

electrochemical cell means having an electrode configuration comprising a plurality of electrodes including a noble metal counter electrode, an Ag/Ag+ reference electrode and a working electrode further comprising a core of the same noble metal as the counter electrode coated with a layer of a conducting polymer having reversible Redox characteristics:

a nonaqueous gelled aprotic electrolyte solution in the electrochemical cell means, said solution comprising an aprotic organic solvent and an electrolyte salt;

adjustable potential electrical source means, to energize said electrochemical cell means at desired potentials, connected across said working and counter electrodes;

potential measuring means connected across said working and reference electrodes; and current measuring means connected across said working and counter electrodes.

10. The electrochemical cell of claim 9 wherein said noble metal is platinum.

11. The sensor of claim 10 wherein said conducting polymer is one selected from the group consisting of polyquinoline and substituted polyquinolines.

12. The sensor of claim 11 wherein said substituted polyquinoline is selected from the group consisting of poly-2,6-(4-phenyl) quinoline, poly-2,6-(4-chlorophenyl) quinoline, poly-2,6-(4-methoxyphenyl) quinoline, and poly-2,6-(N-methyl, 4-phenyl) quinoline.

13. The sensor of claim 12 wherein said substituted polyquinoline is poly-2,6-(4-phenyl) quinoline.

14. The electrochemical cell of claim 9 wherein said nonaqueous gelled aprotic electrolyte solution comprises an aprotic organic solvent selected from the group consisting of γ-butyrolactone and propylene carbonate, and an amount of lithium perchlorate electrolyte.

15. The sensor of claim 14 wherein said conducting polymer is one selected from the group consisting of polyquinoline and substituted polyquinolines.

16. The sensor of claim 15 wherein said substituted polyquinoline is selected from the group consisting of poly-2,6-(4-phenyl) quinoline, poly-2,6-(4-chlorophenyl) quinoline, poly-2,6-(4-methoxyphenyl) quinoline, and poly-2,6-(N-methyl, 4-phenyl) quinoline.

17. The sensor of claim 16 wherein said substituted polyquinoline is poly-2,6-(4-phenyl) quinoline.

18. The sensor of claim 9 wherein said conducting polymer is one selected from the group consisting of polyquinoline and substituted polyquinolines.

19. The sensor of claim 18 wherein said substituted polyquinoline is selected from the group consisting of poly-2,6-(4-phenyl) quinoline, poly-2,6-(4-chlorophenyl) quinoline, poly-2,6-(4-methoxyphenyl) quinoline, and poly-2,6-(N-methyl, 4-phenyl) quinoline.

20. The sensor of claim 19 wherein said substituted polyquinoline is poly-2,6-(4-phenyl) quinoline.

* * * * *